United States Patent [19]

Gawronski

[11] Patent Number: 4,897,346

[45] Date of Patent: Jan. 30, 1990

[54] STABILIZED LIQUID ENZYME COMPOSITION FOR GLUCOSE DETERMINATION

[75] Inventor: Thomas H. Gawronski, Walnut, Calif.

[73] Assignee: Beckman Instruments, Inc., Brea, Calif.

[21] Appl. No.: 886,180

[22] Filed: Jul. 15, 1986

[51] Int. Cl.[4] .................... C12Q 1/54; C12Q 1/48; C12Q 1/32

[52] U.S. Cl. ................................. 435/14; 435/4; 435/15; 435/25; 435/26; 435/27; 435/28; 435/810

[58] Field of Search ................... 435/25–28, 435/810, 14, 26, 4, 7, 15; 436/825

[56] References Cited

U.S. PATENT DOCUMENTS

| | | | |
|---|---|---|---|
| 3,875,011 | 4/1975 | Rubenstein et al. | 435/26 |
| 4,043,872 | 8/1977 | Blakemore et al. | 435/7 |
| 4,169,012 | 9/1979 | Dawson et al. | 435/7 |
| 4,235,961 | 11/1980 | Lundin | 435/8 |
| 4,250,254 | 2/1981 | Modrovich | 435/14 |
| 4,260,678 | 4/1981 | Lepp et al. | 435/7 |
| 4,271,264 | 6/1981 | Modrovich | 435/14 |
| 4,352,881 | 10/1982 | Inagawa et al. | 435/17 |
| 4,387,160 | 6/1983 | Gomez et al. | 435/7 |
| 4,409,326 | 10/1983 | Modrovich | 435/11 |

FOREIGN PATENT DOCUMENTS 0140899  4/1981  Japan ..................... 435/14

OTHER PUBLICATIONS

Flores et al., *Clinical Chemistry*, vol. 32, No. 6 (1986), p. 1105.

Tietz (ed.), *Textbook of Clinical Chemistry*, (1986), pp. 784–787.

*Primary Examiner*—Robert J. Warden
*Assistant Examiner*—Carol A. Spiegel
*Attorney, Agent, or Firm*—Sheldon & Mak

[57] ABSTRACT

A homogeneous liquid enzyme reagent for the quantitative determination of glucose comprises the enzymes hexokinase and glucose-6-phosphate dehydrogenase in a solution of glycerol (30% v/v) in water, and a stabilizer system comprising a heavy metal ion chelating agent. Preferably the stabilizers also comprise an antioxidant and a microbic-control agent. The stabilizers are in sufficient amounts such that the enzyme reagent has a shelf life of at least about two years when stored at a temperature of from 2° to 8° C.

47 Claims, 7 Drawing Sheets

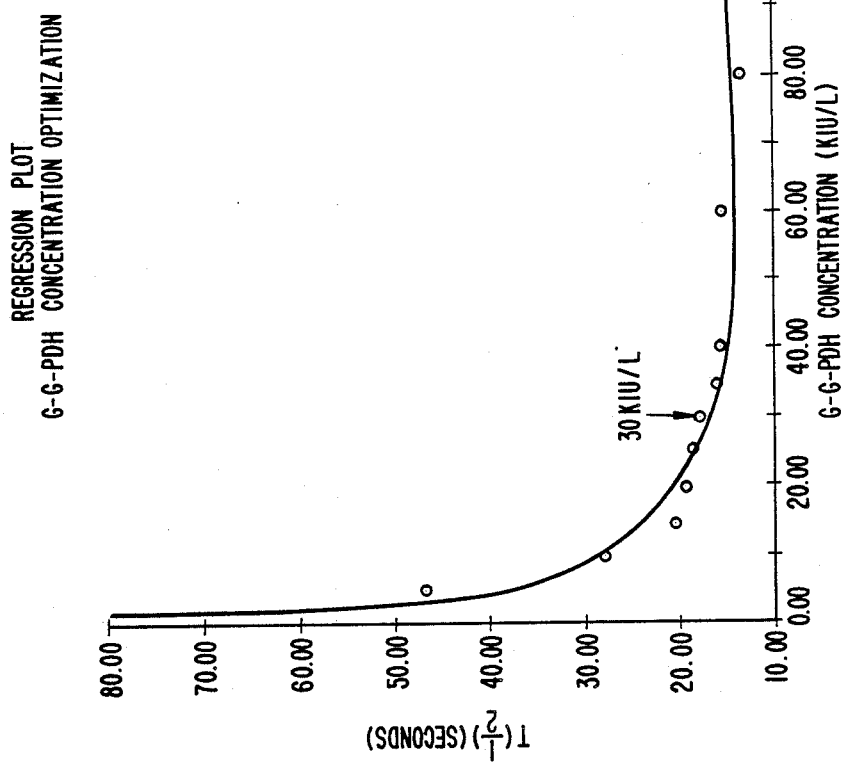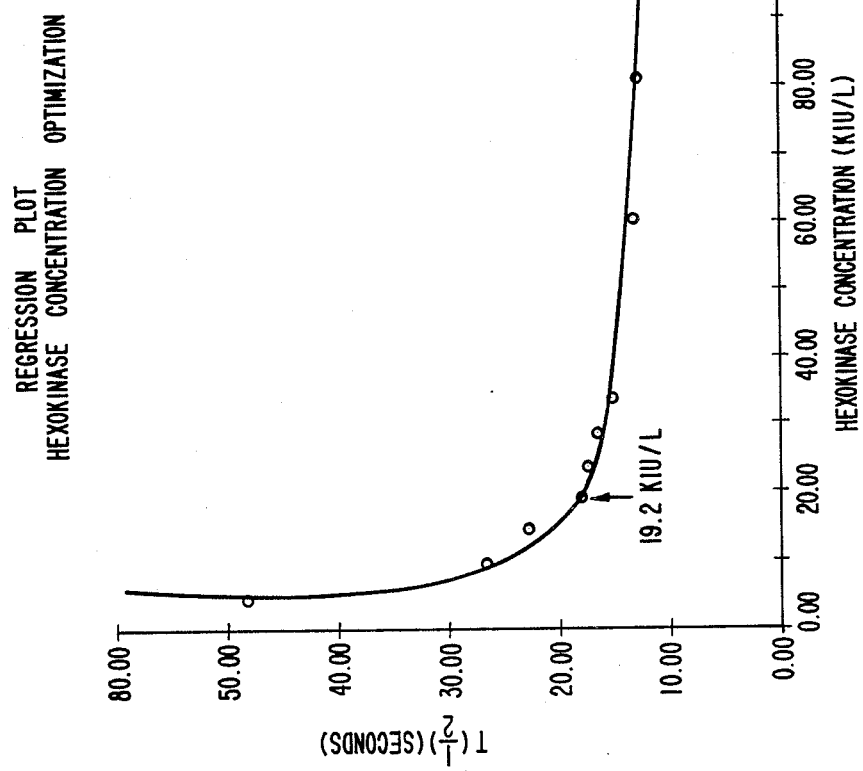

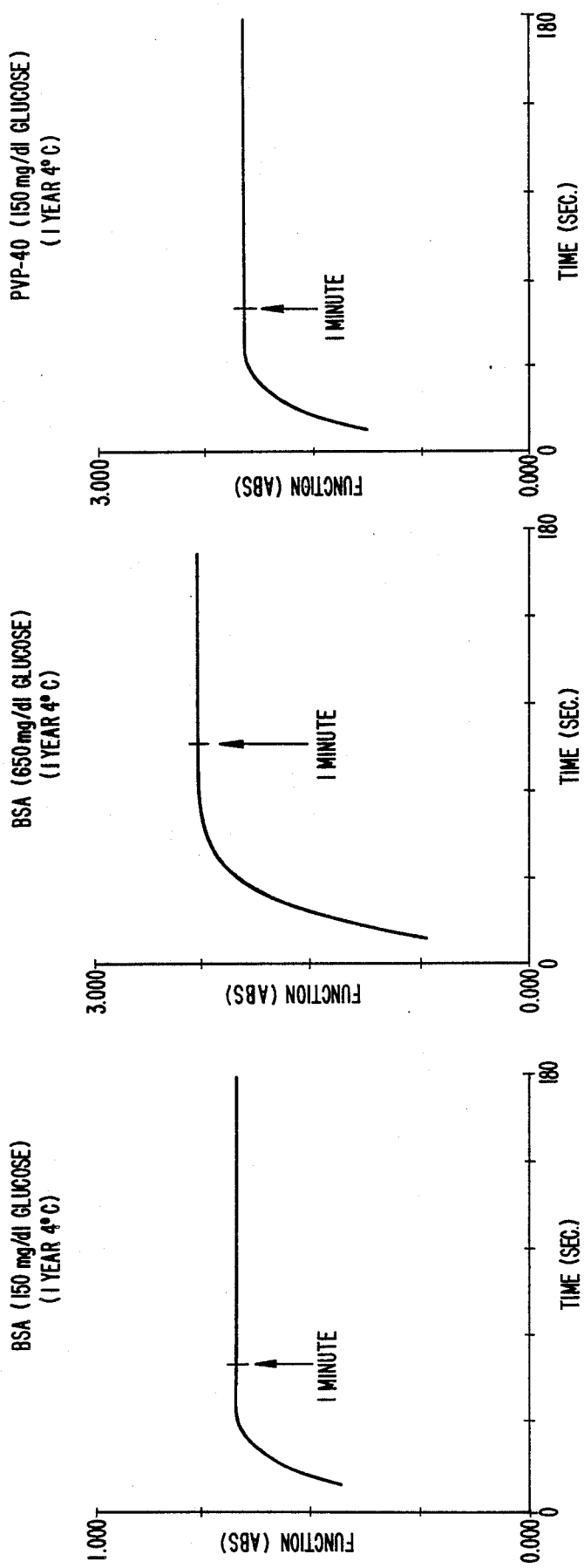

STABILIZED LIQUID ENZYME COMPOSITION FOR GLUCOSE DETERMINATION

BACKGROUND

This invention relates to the use of the enzymes hexokinase and glucose-6-phosphate dehydrogenase in an analytical procedure for determining glucose.

In the determination of enzymes and other biological constituents, the reaction generally involves enzymes, coenzymes and substrates.

Enzymes are complex proteins with large molecular weights, and are usually of unknown chemical structure. They are classified by their substrate specificity, and catalytic activity. Enzymes are biological catalysts, which can catalyze the reaction of a single substrate, or the reaction of a group of similar substrates.

Coenzymes are organic chemicals with well-defined chemical structures. They usually have lower molecular weights than enzymes. They are required for specific enzyme assay or reaction. Coenzymes are detectably changed in their structure and/or atomic composition in the assay. Their reactions are stoichiometric with the substrate. With certain coenzymes having strong absorbence, the creation or disappearance of the absorbing form can be followed photometrically. For example, nicotinamide adenine dinucleotide (NAD) and reduced nicotinamide adenine dinucleotide (NADH) are used in many important clinical assays. Both species have a molecular weight of about 700. NADH absorbs strongly at 340 nm, while NAD does not.

Substrates are organic chemicals of known structure, whose reactions and interactions are catalyzed by enzymes resulting in a change in the substrate's chemical structure, atomic composition, or stereochemistry. In general, substrates are prone to degradation, both chemically and microbiologically. Substrates chemically degrade or hydrolyze in aqueous media, and serve as food for bacteria, fungi and other microorganisms. Typical substrates are glucose, lactate or lactic acid, gluconate and the like.

Because of their high specificity, the use of enzyme determinations has significantly increased during recent years. At present, the greatest limitation on the use of enzyme reagents lies in the unstable nature of the species therein. Numerous labile components are usually involved. To complicate matters, the exact nature of enzymes, as well as the mechanisms of their actions, remains unknown for the most part. Therefore, rigorous quality control measures are required to assure accurate and consistent results. Such measures can be costly.

In the prior art, to ensure strict quality control, emphasis was placed on stabilizing the labile ingredients in the reagents, i.e., to prevent them from degrading. For example, the enzyme or coenzyme can be locked into a solid matrix, either by dry blending, freeze drying, or by locking the chemical structure of the enzyme onto a solid matrix. These methods are expensive, require complicated manufacturing processes, and are less convenient for the user. Product uniformity is difficult to maintain with solid reagents. For example, many commercial freeze dried reference sera list an acceptable bottle-to-bottle variation of enzyme constituents at ±10% of the mean. More importantly, the user has to bear the burden of assuring the quality control in the dilution and use of the solid reagent. Because of these quality control problems with solid enzyme or coenzyme reagents, and because of the convenience factor, users generally prefer liquid, easy-to-use, and homogeneous reagents over solid (e.g. lyophilized) compositions.

Glucose/HK/G-6-PDH Chemistry

The symbols used herein represent the following constituents:

ADP = adenosine-5'-diphosphate
ATP = adenosine triphosphate
HK = hexokinase
NAD = nicotinamide-adenine dinucleotide
NADH = nicotinamide-adenine dinucleotide, reduced
G-6-PDH = glucose-6-phosphate dehydrogenase
G-6-P = glucose-6-phosphate The following reactions illustrate the determination of glucose by using the coenzymes ATP and NAD, in the presence of the enzymes HK and G-6-PDH.

Primary Reaction $$\text{GLUCOSE} + \text{ATP} \xrightarrow{\text{HK, Mg}^{++}} \text{G-6-P} + \text{ADP} \quad (1)$$

Measuring Reaction $$\text{G-6-P} + \text{NAD} \xrightarrow{\text{G-6-PDH}} \text{NADH} + \text{6-PHOSPHOGLUCONATE} + \text{ADP} \quad (2)$$

In the above reaction scheme, the enzyme which causes the primary reaction is HK, and the enzyme which causes the measuring reaction is G-6-PDH. The glucose is determined by measuring the rate at which NADH is formed in the measuring reaction. The above reaction scheme is used extensively in clinical assays, as elevated glucose concentration in body fluids, such as serum, plasma, whole blood, cerebrospinal fluids, and urine, etc., has been shown to be associated with diabetes.

In the quantitative determination of glucose, the above reactions generally are allowed to go to completion. The amount of NADH formed correlates with the amount of glucose in the test sample. NADH absorbs strongly at 340 nm while the other reactants and products do not. The amount of NADH formed, and thus the amount of glucose in the test sample, can be followed at 340 nm with a spectrophotometer. Enzyme activity is generally measured in terms of International Units (IU). One International Unit is defined as the amount of enzyme which will catalyze the conversion of one micromole of substrate per minute under specified conditions. Under glucose assay conditions, sufficient enzymes (HK and G-6-PDH) and coenzyme (ATP and NAD) are added to ensure relatively rapid reaction rates. Preferably the reactions for the above assay go to substantial completion within minutes, more preferably within about ten minutes.

Because of the labile nature of the ingredients involved in the above described glucose assay, generally components of the determinative reagents are stored separately, and are mixed only shortly before the assay is performed. For example, commercially available reagents for the glucose assay above generally come as a two-reagent package, consisting of a coenzyme reagent and an enzyme reagent. The coenzymes are not as labile as the enzymes, and generally are kept in solution for convenience reasons. The liquid coenzyme reagent for the glucose assay generally contains both of the coenzymes ATP and NAD, a magnesium salt (generally magnesium acetate), preservatives, and a buffer for maintaining a pH at about 7.5, which is the preferred pH for performing the glucose assay.

The problem with stability is a critical one when the enzymes HK and G-6-PDH are concerned. Traditionally, the enzyme reagent for the glucose assay comes in dry-pack or lyopholized form. The dry enzymes are put into solution shortly before the assay is performed.

Liquid HK/G-6-PDH Enzyme Stabilization

Because of all the disadvantages of solid enzyme reagents, attempts have been made to stabilize the enzymes KH and G-6-PDH in solution. One common practice is the use of a high concentration (e.g. 3 molar) of ammonium sulfate as a preservative. The enzymes HK and G-6-PDH are first placed in aqueous solution, and then the ammonium sulfate is added. The stability of this liquid enzyme reagent is satisfactory, but this system suffers serious drawbacks. In the first place, sulfate is a well known inhibitor for the reactions in the glucose assay described above. In order to make the reactions proceed at acceptable rates, it is necessary to use relatively large quantities of the enzymes (HK and G-6-PDH) in order to overcome the inhibition. This adds to the cost. Secondly, the enzymes precipitate out of solution once the ammonium sulfate is added. Thus this liquid reagent is not homogeneous, but is really a "suspension" reagent. Even with vigorous mixing, it is difficult to obtain reproducible results with this suspension enzyme reagent. It is hard to measure (e.g. by pipeting) exact quantities of the precipitated enzyme. Moreover, this suspension enzyme reagent must be well mixed before it can be used. This requirement is an impediment against automation. Few, if any, spectrophometers currently in use are equipped to premix component reagents. Further, because of the strong inhibitory effects of ammonium sulfate, it is necessary to use a minimal volume of this suspension enzyme reagent. Typically, the enzyme reagent and coenzyme reagent are mixed in a proportion of 1:100 or more. The small volume of this heterogeneous enzyme reagent used makes it even harder to get reproducible assay results.

It has also been suggested that enzymes such as HK and G-6-PDH can be stabilized in an aqueous medium, i.e. prevented from degrading, by adding 10-50% v/v of an aqueous miscible polyol organic solvent (such as glycerol). However, it was found that in practice this approach often does not work. The enzymes still deteriorate over time and the polyol-stabilized liquid enzyme reagent has a relatively short shelf-life even at the recommended storage temperature range of 2° to 8° C. (enzyme degradation increases rapidly at elevated temperatures). Even if polyol solvents have any stabilizing effect, the degree of stabilization is not acceptable. The degradation is demonstrated by a slow down of the glucose assay reactions above.

The degradation of the enzymes HK and G-6-PDH can show up as lot-to-lot variations, especially with reagents stored for different periods of time. This variation can adversely affect the reliability of the glucose assay.

Therefore there is a need for a homogeneous liquid HK and G-6-PDH enzyme reagent for glucose determination, with a long shelf-life, which gives reproducible assay results, and which gives quick glucose end point determination.

SUMMARY

The present invention satisfies the above needs. The invention relates to a homogeneous liquid enzyme reagent with a long shelf life, the enzyme reagent for use for the quantitative determination of glucose in a glucose assay using adenosine triphosphate and nicotinamide-adenine dinucleotide as coenzymes, the coenzymes being in excess, the enzyme reagent when initially prepared comprising:

(a) at least about 68% v/v of water;
(b) a water-miscible polyol organic solvent in an amount of from about 20 to about 40% v/v;
(c) hexokinase enzyme;
(d) glucose-6-phosphate dehydrogenase enzyme;
(e) a stabilizer system comprising a heavy metal ion chelating agent in a sufficient amount of at least about 0.5 mM such that the enzyme reagent has a shelf life of at least two years when stored at a temperature in the range of from about 2° to about 8° C. Preferably the chelant is EDTA. Preferably the stabilizer system also comprises an antioxidant and a microbic-control agent. The antioxidant can be bovine serum albumin (BSA), or a combination of polyvinylpyrrolidone-40 (PVD-40) and N-acetyl cysteine (NAC). The microbio-control agent can be sodium azide.

Preferably the enzyme reagent is used in conjunction with a coenzyme reagent containing magnesium ions and the coenzymes adenosine triphosphate and nicotinamide-adenine dinucleotide. When the enzyme reagent is mixed with the coenzyme reagent and a test sample containing glucose to form an assay reaction mixture, preferably the amount of the chelating agent from the enzyme reagent is no more than about half of the magnesium ions from the coenzyme reagent, more preferably no more than about one-tenth.

DRAWINGS

These and other features, aspects and advantages of the present invention will become better understood with reference to the following description, appended claims, and accompanying drawings where:

FIGS. 7–10 show the effect of changes in the concentration of HK, G-6-PDH, ATP, and NAD, respectively, on the time of one-half reaction T(½), while the concentrations of other components are kept constant; and FIGS. 11–15 are reaction profiles of glucose assays using the enzyme reagent of the subject invention stored at 4° C. for periods of time varying from 1 to 2½ years.

DESCRIPTION

Figure 2:
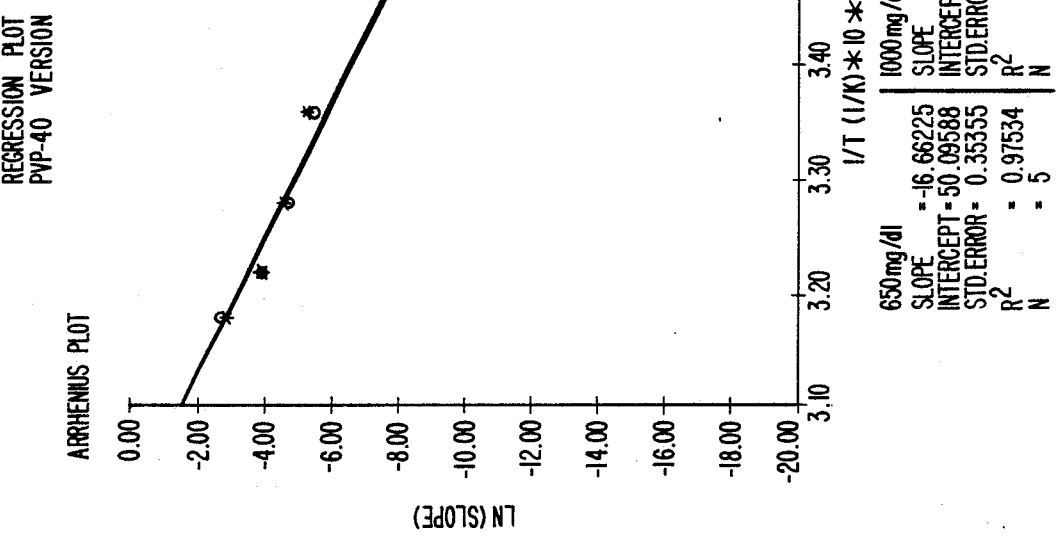
FIGS. 1 and 2 are Arrhenius plots of the rate of decay (slope) versus the reciprocal of temperature for the BSA and PVP-40 versions of the enzyme reagent of the subject invention.

It is well known that the enzyme hexokinase and glucose-6-phosphate dehydrogenase are highly labile, and both degrade over time, especially at elevated temperatures. It was previously suggested that the presence of a water-miscible organic polyol solvent, such as glycerol, can stabilize these enzymes in aqueous solution.

However, it was found that attempted stabilization with organic polyol solvents gives inconsistent results, especially when commercial grade solvents are used. It was also discovered that commercial grade organic polyol solvents, e.g. glycerol, especially those which have been improperly handled and/or stored, and the water used in making up the enzyme reagent, can both contain contaminants which actually promote the degradation of the enzymes HK and G-6-PDH.

It was discovered that a certain stabilizer system in the presence of an organic polyol solvent can improve the stability of a homogeneous liquid enzyme solution containing the enzymes HK and G-6-PDH. Suitable components for the stabilizer system are selected on the basis of their enzyme stabilization efficiency, non-interference with the glucose enzyme reactions, cost, solubility, lack of odor, and ease of disposal.

The stabilizer system comprises a heavy metal ion chelating agent. This discovery is surprising, in view of the fact that magnesium ions are required to catalyze the primary reaction step between glucose and ATP, and magnesium ions are generally included as a component of the coenzyme reagent. The chelating agent would be expected to render the magnesium ions ineffective as a catalyst, and adversely affect the glucose assay. Suitable heavy metal ion chelating agents include, for example, ethylenediamine tetraacetic acid (EDTA).

Preferably the stabilizer system also comprise an antioxidant. Suitable antioxidants include, for example:
1. L-cysteine ethyl ester hydrochloride (CEE)
2. N-acetyl-cysteine (NAC)
3. DL-homocysteine thiolactone hydrochloride (HCTL)
4. L-cysteine
5. Mercaptoethanol (ME)
6. Dithiothreitol (DTT)
7. Dithioerythritol (DTE)
8. Aminoethylisothiouronium bromide (AET)
9. Glutathione (GSH)
10. Thioglycolic acid (TGA)
11. N-Guanyl-L-cysteine
12. N-Guanyl-DL-isocyanate
13. N-Acetyl-S-guanyl-L-cysteine
14. N-Acetyl-S-benzyl-L-cysteine
15. N,S-Diguanyl-L-cysteine
16. S-Carbamoyl-L-cysteine
17. S-Carboxymethyl-L-cysteine
18. L-Thiazolidine-4-carboxylic acid
19. S-Guanyl-L-cysteinehydantoin
20. S-Acetylguanyl-DL-cysteineazlactone
21. 2-Imino-L-cysteinehydantoin
22. N-Acetyl-DL-homocysteinethiolactone
23. 1,3 Dimercapto-2-propanol
24. 2,3 Dimercapto-1-propanol
25. 1,2 Dimercapto-ethane
26. L-Cysteinemethyl ester
27. L-Cysteineethyl ester
28. N-Acetyl-DL-isocysteine
29. Polyethyleneglycol dimercaptoacetate
30. Thioglucose
31. Thioglycerol
32. Polyvinylpyrrolidone-40 (PVP-40)
33. Bovine Serum Albumin (BSA)

Preferably the stabilizer system also comprise a microbio-control agent, such as a microbiostat or a microbiocide. Suitable microbio-control agents include, for example, sodium azide, benzoic acid, phenol, thymol, or pentachlorophenol.

Preferably in the assay reaction mixture the amount of chelating agent from the enzyme reagent is no more than about one half the amount, more preferably no more than one-tenth the amount, of the magnesium ions from the coenzyme reagent on a molar basis.

As indicated above, the glucose assay reactions are allowed to go to substantial completion. The measuring reaction generates NADH, which presence can easily be followed by using a spectrophotometer. The point of substantial completion of the assay reactions, or the "end point", is generally defined as the point at which the NADH concentration is at least about 98% of the final equilibrium NADH concentration. The end point can be observed on a scan of the spectrophotometer reading (at 340 nm) over time. The absorbance, and thus the NADH concentration, increases initially, but gradually levels off to a relatively constant value. The point at which the absorbance first levels off (greater than 98% reaction completion) can be taken as the end point.

It is desirable that the end point for the glucose assay be reached in as brief a time as possible. Quick end point determination is especially important when the glucose assay is automated, as tying up costly serum analyzers can be expensive.

The enzyme reagent of this invention, which incorporates the stabilizer system described above, can have a shelf life of two years or more. The shelf life of an enzyme reagent is generally defined as the period of time within which the enzyme reagent gives acceptable performance in a standard glucose assay. The standard glucose assay is defined as mixing one part of a glucose enzyme reagent with 10 parts of a glucose coenzyme reagent to form a combined reagent, and then mixing 100 parts of the combined reagent with one part of a test sample containing glucose, to form an assay reaction mixture. All parts are by volume.

Specifications for HK/G-6-PDH enzyme reagents for glucose assays are generally defined as requiring that an end point be reached within a specified time period (e.g. ten minutes), provided that the glucose concentration in the test sample is within a range of concentration for which the enzyme reagent is operable. This concentration range is called the "dynamic range" of the enzyme reagent. Shelf life for the enzyme reagent of the present invention is defined as giving an end point in ten minutes or less for a dynamic range of 10 to 500 mg glucose per deciliter (mg/dL) in the test sample for the standard glucose test above. More preferably the end point is reached in five minutes or less. Most preferably the end point is reached in two minutes or less.

In everyday glucose assays, it is common practice to use substantially excess amounts of coenzymes in the assay reaction mixture relative to the maximum amount of glucose in the dynamic range for the enzyme reagent used. Preferably the mole ratio of ATP to glucose in the reaction mixture is in the range of from about 3:1 to about 14:1. Preferably the mole ratio of NAD to glucose in the reaction mixture is in the order of 5:1 or more. These ratios are computed using the upper limit of the glucose concentration in the dynamic range of the enzyme reagent. These coenzyme concentration ranges are assumed in the above definition of shelf life for the enzyme reagent of this invention. Therefore the critical variable affecting the rate of the measuring reaction at any given glucose concentration in the assay reaction mixture is the activity of the enzymes in the enzyme reagent. Adding larger amounts of enzymes would theoretically increase the reaction rate and result in a quicker end point determination. However, there are balancing considerations. The cost of the enzymes militates against using amounts in substantial excess. Moreover, contaminants and inhibitors are known to be present in purified forms of hexokinase and glucose-6-phosphate dehydrogenase. For example, it is known that the contaminant phosphohexose isomerase can be present in purified hexokinase. This contaminant changes glucose-6-phosphate (an intermediate in the glucose assay) into fructose-6-phosphate. The glucose assay results would thus appear artificially low. To limit the quantities of such contaminants and inhibitors, it is desirable to use smaller amounts of the enzymes HK and G-6-PDH, so as to minimize the deleterious effects of the contaminants and inhibitors.

Shelf life depends significantly on the temperature at which the enzyme reagent is stored. The enzymes HK and G-6-PDH degrade very rapidly at elevated temperatures. The accepted practice is to store the enzyme reagent at a temperature between about 2° to about 8° C., most preferably at about 4° C.

For the glucose assay reaction mixture proportions described above, for a dynamic range of glucose concentration with an upper limit of 500 mg/dl, as shown in example 3 and FIGS. 7 and 8 below, the optimal concentration ranges for HK and G-6-PDH in the enzyme reagent are as follows: In general, the lower end of the range is limited by the time within which the end point can be reached, and the upper end of the range is limited by cost. The concentration ranges below assume that a 10 minute end point is preferred, and that a 2 minute end point is most preferred. The preferred concentration range for HK in the assay reaction mixture in the enzyme reagent is from about 6 to about 80 KIU per liter, more preferably from about 10 to about 60 KIU per liter, most preferably from about 15 to about 35 KIU per liter. These concentrations correspond to a preferred concentration range for HK in the assay reaction mixture of from about 0.54 to about 7.2 KIU per liter, more preferably from about 0.9 to about 5.4 KIU per liter, most preferably from about 1.35 to about 3.15 KIU per liter. The corresponding optimal concentration range for G-6-PDH in the enzyme reagent is from about 3 to about 60 KIU per liter, more preferably from about 15 to about 40 KIU per liter, most preferably from about 20 to about 35 KIU per liter. These concentrations correspond to a preferred concentration range for G-6-PDH in the assay reaction mixture of from 0.27 to about 5.4 KIU per liter, more preferably from about 1.35 to about 3.6 KIU per liter, most preferably from about 1.8 to about 3.15 KIU per liter.

Another measure of the stability of the glucose HK/G-6-PDH enzyme reagent is the time of one-half reaction T($\frac{1}{2}$), which is the time at which the measuring reaction in the glucose assay is half complete. This can be determined by a comparison of the final and initial absorbance at 340 nm for the glucose assay. The reaction time at which the absorbance is halfway between the initial and final absorbances is the time of one-half reaction. As the coenzyme concentrations are in excess, the time of one-half reaction is dependent upon the concentrations of the glucose and the undegraded enzymes in the assay reaction mixture. During the shelf life of the enzyme reagent, preferably the time of the one-half reaction for a glucose assay using the aged enzyme reagent of the subject invention is no more than about 1.5 times the time of one-half reaction for an identical assay using the enzyme reagent when it was initially made.

For the glucose assay above, times of one-half reactions of 30 seconds and 1$\frac{1}{2}$ minutes correspond roughly to end points at 3 and 10 minutes, respectively.

All of the discussions concerning glucose assays herein assume that the assays are performed at the optimal temperature and pH for such assays. It is generally accepted that the temperature should be about 37° C., and the pH should be about 7.5.

In a preferred version of the enzyme reagent of the present invention, the enzyme reagent when initially prepared comprises:
  (a) at least about 60% v/v of water;
  (b) a water miscible polyol organic solvent in an amount of from about 20 to about 40% v/v;
  (c) hexokinase enzyme in an amount of from about 6 to about 80 KIU per liter;
  (d) glucose-6-phosphate dehydrogenase enzyme in an amount of from about 3 to about 60 KIU per liter;
  (e) a stabilizer system comprising:
    (i) a heavy metal ion chelating agent, being ethylenediamine tetraacetic acid (EDTA) in an amount of from about 0.5 to about 5 mM;
    (ii) an antioxidant, being bovine serum albumin in an amount of from about 2 to about 8 g per liter;
    (iii) a microbio-control agent, being sodium azide in an amount of from about 0.25 to about 1.0 g per liter;
  (f) TRIS-HCl buffer, in an amount of from about 0.05 to about 0.2 mM;

wherein the pH of the enzyme reagent is preferably adjusted to about 7.5 with glacial acetic acid.

In another preferred version of the enzyme reagent, bovine serum albumin (BSA) is replaced by polyvinylpyrrolidone-40 in an amount of from about 2 to about 8 g per liter, and N-acetyl cysteine in an amount of from about 0.4 to about 1.6 g per liter. All the other ingredients remain the same.

The above preferred versions of the enzyme reagents are suitable for use with a dynamic range of glucose concentration preferably from 10 to 1,000 mg/dL, most preferably from 10 to 500 mg/dL, in the standard glucose assay described above.

The enzyme reagent of this invention is designed to be used with a homogeneous coenzyme reagent comprising:
  (a) at least about 80% v/v of water;
  (b) a water-miscible polyol organic solvent in an amount of from about 5 to about 20% v/v;
  (c) adenosine triphosphate coenzyme; and
  (d) nicotinamide-adenine dinucleotide coenzyme.

Preferably the coenzyme reagent also contains Mg++ ions. Preferably the coenzyme is buffered with TRIS-HCl, and its pH is adjusted to about 7.5. The coenzyme reagent can also contain a microbio-control agent.

Figure 10:
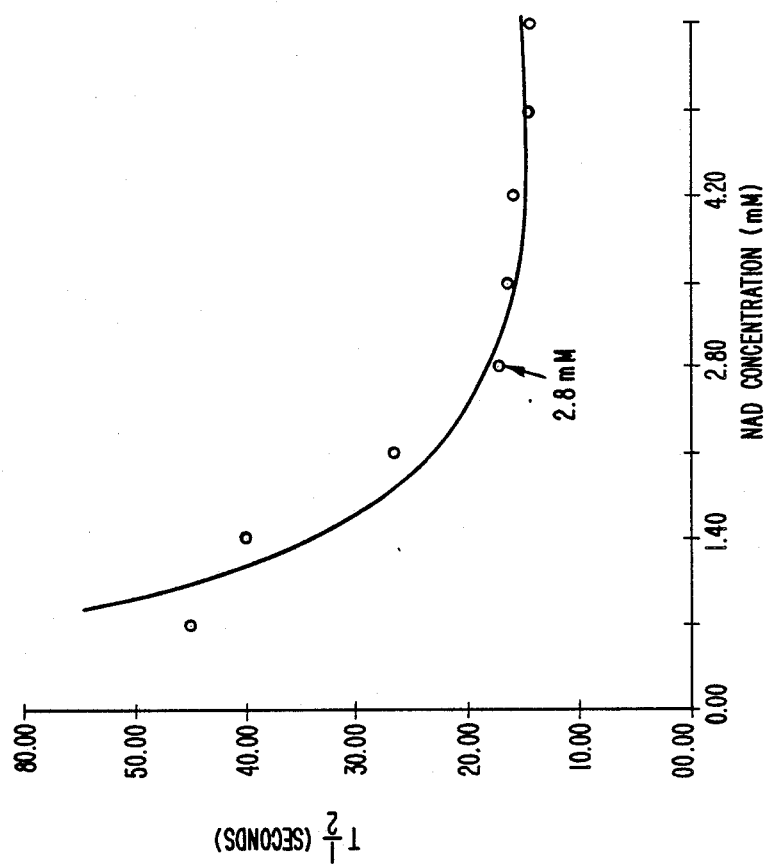
Figure 9:
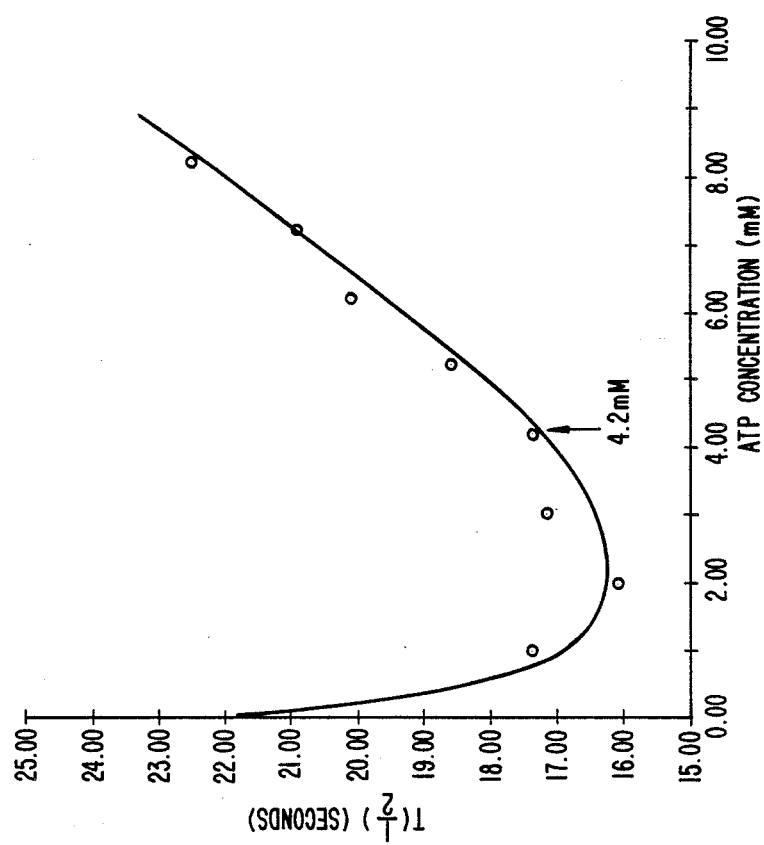
Figure 15:
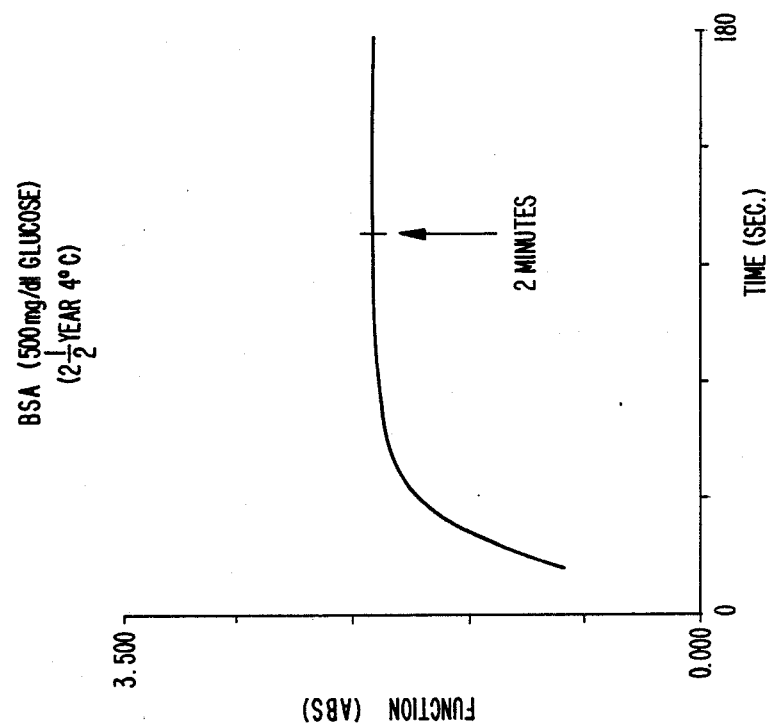
Figure 14:
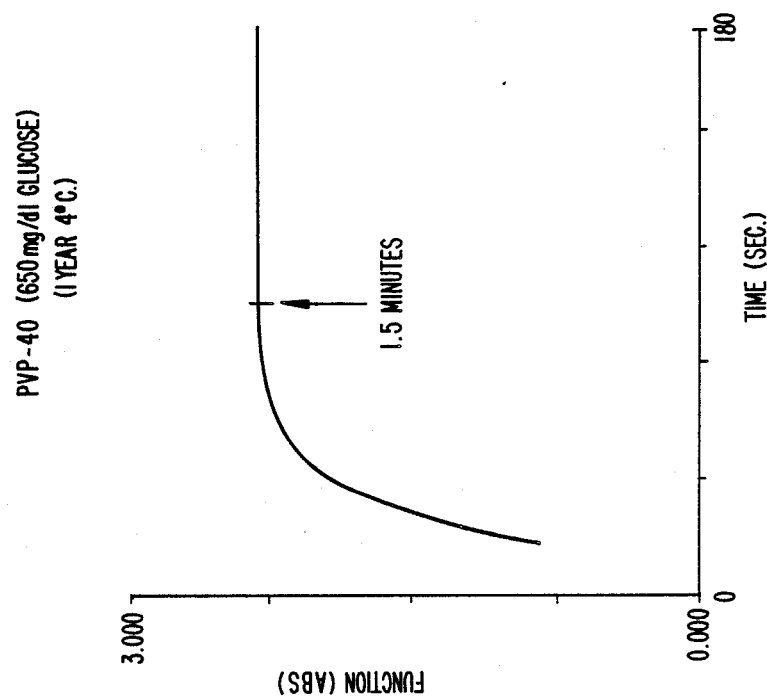

The optimal amounts of the coenzymes adenosine triphosphate and nicotinamide-adenine dinucleotide in the coenzyme reagent are shown in FIGS. 9 and 10 below. The preferred concentration ranges in the coenzyme reagent of the 2 coenzymes are: ATP, from about 0.3 to about 0.6 mM, more preferably from about 1 to about 4.2 mM; NAD, from about 1.4 to 4.2 mM, more preferably about 2.5 to about 3.5 mM. In the standard glucose assay reaction mixture, the corresponding concentration of the coenzymes would be: ATP, from about 0.3 to about 5.4 mM, more preferably from 0.9 to about 3.8 mM; NAD, from about 1.3 to about 3.8 mM, more preferably from about 2.2 to about 3.2 mM. The molar ratio of ATP to glucose in the assay reaction mixture, at a glucose concentration of 500 mg/dL in the test sample, would preferably be in the range of about 1:1 to about 20:1, more preferably between 3:1 to about 14:1. The molar ratio of NAD to glucose in the assay reaction mixture, at a glucose concentration of 500 mg/dL in the test sample, would preferably be between 5:1 and 13:1, more preferably between 9:1 and 11:1.

EXAMPLES

A. Suppliers

In the following examples, unless otherwise specified, the following chemicals were used:

Glucose standards are available from New England Reagent Laboratory (NERL) of East Providence, R.I. Glucose, benzoic acid, glycerol, magnesium acetate, sodium azide, glacial acetic acid, and EDTA are available from J. T. Baker Chemical Co. of Phillipsburg, N.J. TRIS-HCl buffer, BSA, PVP-40 and N-acetyl cysteine are available from Sigma Chemical Co. of St. Louis, Mo. The coenzymes ATP and NAD, and the enzymes HK and G-6-PDH are available from Boehringer Mannheim Biochemicals of Indianapolis, Ind.

B. Formulations

In the following examples, unless as otherwise specified, the following formulations were used:

(1) Glucose Standards

Two types of glucose standards were used:

(a) Laboratory Prepared Glucose Standards

Solid glucose was placed in a drying oven (80° C.) for 24 hours. It was then cooled in a desicator. Standard glucose solutions of various preset concentrations were prepared gravimetrically from this dried glucose. The standards also contain 0.2% benzoic acid as a preservative.

(b) NERL Glucose Standards

NERL glucose standards were used as purchased. Deionized water was used to dilute the standards where necessary (e.g. from 50 mg/dL to 25 mg/dL). NERL glucose standards come in the following concentrations: 50, 100, 200, 400 and 750 mg/dL.

(2) Coenzyme Solution

| Glycerol | 100 ml |
| TRIS-HCl | 12.0 g |
| Magnesium Acetate | 2.22 g |
| Sodium Azide | 0.5 g |
| Glacial Acetic Acid (to pH 7.5) | 4.6 ml |
| ATP | 2.526 g |
| NAD | 2.026 g |

The components were diluted to 1 liter with deionized water.

(3) Enzyme Solution (a) BSA Version:

| (a) BSA Version: | |
|---|---|
| Glycerol | 300 ml |
| TRIS-HCl | 12.11 g |
| EDTA (free acid) | 0.29 g |
| Glacial Acetic Acid (to pH 7.5) | 4.28 g |
| BSA | 4.0 g |
| HK | 19.2 KIU/L |
| G-6-PDH | 30 KIU/L |

The components were diluted to 1 liter with deionized water.

(b) PVP-40 Version

Same as BSA version except BSA was replaced by:

| Polyvinylpyrrolidone-40 (PVP-40) | 4.0 g |
| N-Acetyl cysteine (NAC) | 0.815 g |

C. Instrumentation

A Beckman Instruments, Inc. Model DU-7 Spectrophotometer was used in the following examples. The instrument settings were as follows:

| Mode | Timedrive |
|---|---|
| Function | [Abs] |
| Wavelength | 340 nm |
| Rate | [1200] |
| Total Time | 5 minutes |
| Upper | 3 |
| Lower | 0 |
| Temperature | 37° C. |

A Roche Analytical COBAS BIO clinical analyzer was also used in this study. The instrument settings used in this study were as follows:

| 1. | UNITS | mg/dL |
|---|---|---|
| 2. | CALCULATION FACTOR | 0 |
| 3. | STANDARD 1 CONC | 150 |
| 4. | STANDARD 2 CONC | 150 |
| 5. | STANDARD 3 CONC | 150 |
| 6. | LIMIT | 0 |
| 7. | TEMPERATURE | 37° C. |
| 8. | TYPE OF ANALYSIS | 1 |
| 9. | WAVELENGTH [nM] | 340 |
| 10. | SAMPLE VOLUME [uL] | 3 |
| 11. | DILUENT VOLUME [uL] | 10 |
| 12. | REAGENT VOLUME [uL] | 300 |
| 13. | INCUBATION TIME [SEC] | 180 |
| 14. | START REAGENT VOLUME [uL] | 0 |
| 15. | TIME OF FIRST READING [SEC] | 180 |
| 16. | TIME INTERVAL [SEC] | 180 |
| 17. | NUMBER OF READINGS | 1 |
| 18. | BLANKING MODE | 1 |
| 19. | PRINTOUT MODE | 1 and 3 |

D. Procedures (1) Thermolysis of Enzyme Solution

Samples of the enzyme solution were bottled in labelled barex cartridges, and placed into incubators set at various constant temperatures. The degradation was monitored at each temperature by using the incubated enzyme reagents in the glucose assay below at different incubation times. Incubation at raised temperatures accelerates degradation, and approximates degradation at lower tempeatures over a longer period of time.

(2) Glucose Assay (a) DU-7 Spectrophotometer—The reagent was first mixed in a cuvette as follows: 0.181 mL (1 part) enzyme solution and 1.81 mL (10 parts) coenzyme solution were mixed. The combined reagent was incubated at 37° C. for four minutes. Twenty microliters (20 uL) of sample was then added to the cuvette to start the reaction. At the same time the sample was added to the cuvette, the RUN button on the DU-7 was pressed to start the spectrophotometer. Duplicate samples were run.

(b) COBAS BIO—After programming the settings above, two replicate samples were placed into sample cups. The Glucose reagent Enzyme and Coenzyme components were mixed in a COBAS BIO reagent tray as follows: 1 mL of Enzyme component and 10 mL of coenzyme component. Beckman ASTRA Calibration Standard (Part No. 888384) was placed into the standard compartment of the tray.

In both of the above assay procedures, the volume proportion was 1:10 of enzyme solution to coenzyme solution in the combined reagent. The combined reagent to test sample ratio was 100:1 by volume.

E. Calculations (1) Time of One-Half Reaction

Time of one-half reaction $T(\frac{1}{2})$ is the time at which the measuring reaction in the glucose assay is half complete based on the final and initial absorbence at 340 nm. This was calculated as follows. After completing the reaction, the absorbance at 210 seconds was determined from the results on the DU-7. The initial absorbance was subtracted from the final absorbance, and the difference was divided by two to give the absorbance at one-half reaction. The corresponding time (as read from the DU-7 spectrophotometer results) for this absorbance is the time of one-half reaction, $T(\frac{1}{2})$.

(2) Linearity Study

The degree of degradation of the enzyme solutions is related to the change in the time of one-half reaction $T(\frac{1}{2})$. Results from the COBAS BIO were tabulated from both Printout mode 1 and 3. From Printout mode 3 the delta absorbance for each sample was calculated by taking the difference between the first reading and the final abosrbance. The final absorbance was measured after 3.5 minutes. This result was plotted against the standard concentration in mg/dL.

EXAMPLE 1

Stability Study of HK/G-6-PDH Enzyme Solutions Under Accelerated Degradation Conditions Samples of the BSA version and PVP-40 version of the enzyme solution were subjected to thermolysis at the following temperatures: 4°, 15°, 25°, 32°, 37° and 41° C. The activity of the enzyme solutions were studied using the glucose assay described above, using laboratory prepared glucose standards containing 650 and 1,000 mg/dL glucose, respectively. These relatively high glucose levels were chosen because enzyme degradation has more serious deleterious effects at higher glucose levels. Also, these high glucose concentrations give easy to measure $T(\frac{1}{2})$'s.

Figure 1:
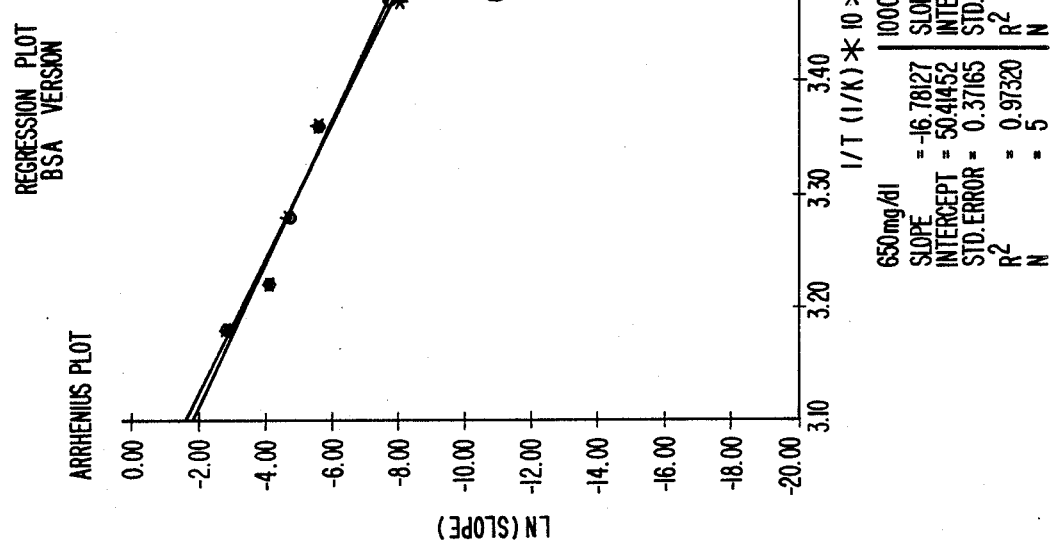

The results of the stability study were presented in FIGS. 1 and 2, which represent the results for the BSA and PVP-40 versions of the enzyme solution, respectively. Both FIGS. 1 and 2 are Arrhenius plots reflecting the relationship between the rate of decay (slope) versus the reciprocal of the temperature (in °K). The slopes were measured at each temperature by plotting the linear function $\ln[1/T(\frac{1}{2})]$ versus time (in days). The two lines shown on each Arrhenius plot represent the two glucose concentrations (standards) used for these studies.

Table 1 gives the projected shelf lives of the enzyme solutions, based on the linear regressions defined to reflect the time, at each temperature, to reach of $T(\frac{1}{2})$ of 25 seconds. This $T(\frac{1}{2})$ roughly corresponds to a time of reaction completion at about 3 to 4 minutes. Calculations were based on an initial $T(\frac{1}{2})$ of 19 seconds for 650 mg/dL and 22 seconds for 1,000 mg/dL.

TABLE 1

| Projected Shelf Life for Stabilized HK/G-6-PDH | | | | |
|---|---|---|---|---|
| Upper Limit of Glucose | BSA version | | PVP-40 Version | |
| Dynamic Range | 650/mg/dL | 1,000 mg/dL | 650/mg/dL | 1,000 mg/dL |
| Temperature °C. | | | | |
| 4 | 16.9 years | 6 years | 15.1 years | 9.3 years |
| 15 | 1.9 years | 10 months | 1.7 years | 1.0 years |
| 25 | 3.6 months | 1.8 months | 3.3 months | 1.9 months |

EXAMPLE 2

Linearity Studies of HK/G-6-PDH Enzyme Solutions

Figure 3:
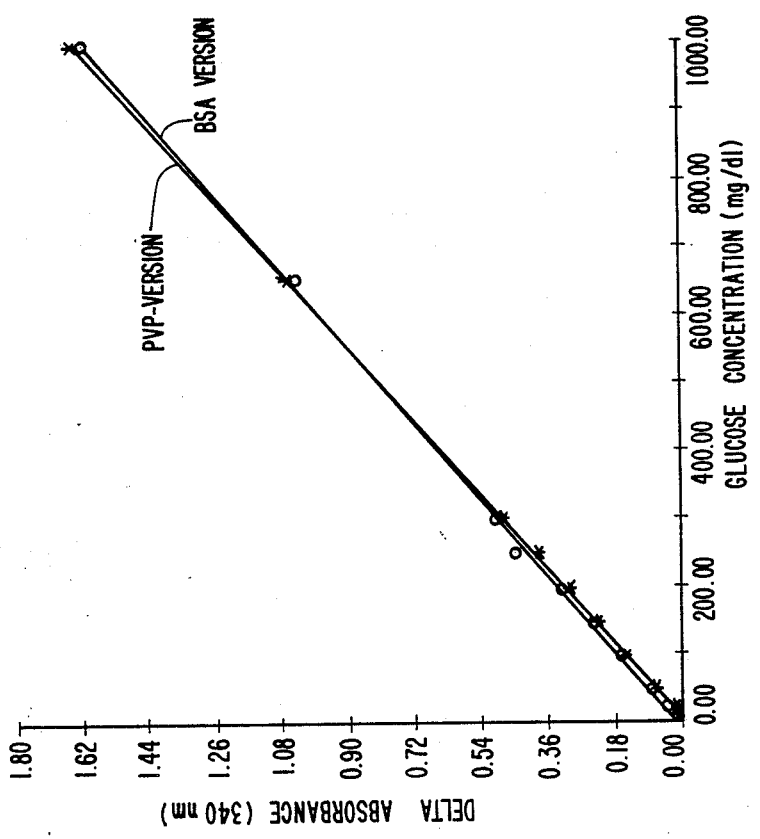

Freshly prepared enzyme solutions (day 0, 4° C.) were used in glycose assays, using laboratory prepared glucose standards of 25, 50, 100, 150, 200, 400, 500, 650 and 1,000 mg/dL, respectively. The difference between the initial and final absorbances (Δ Abs) was plotted against glucose concentration in FIG. 3. The initial absorbance was about 0.06 for both versions of the enzyme solution. Good linearity is shown for both the BSA and PVP-40 versions of the enzyme solution stored at 4° C. on day 0.

Figure 4:
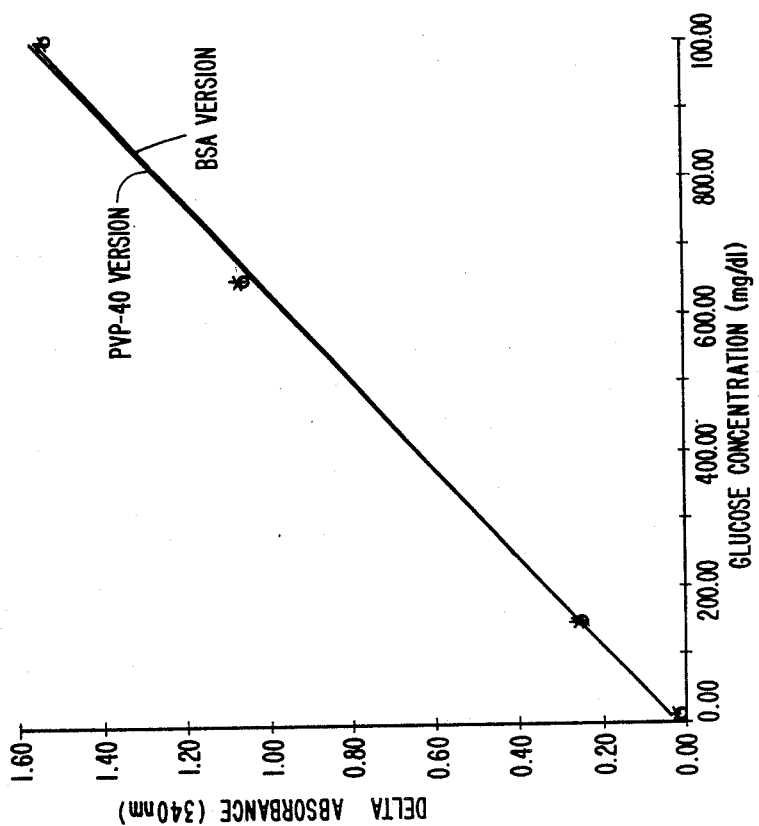
FIGS. 3–6 are linearity plots of the enzyme reagent of the subject invention when (a) initially made; (b) stored at 25° C. for 106 days; (c) stored at 4° C. for one year; and (d) stored at 4° C. for 2½ years, respectively.

The same procedure was repeated for the two versions of the enzyme solution, both stored at 25° C. for 106 days. The glucose concentrations in the laboratory prepared glucose standards were 25, 150, 650, and 1,000 mg/dL respectively. The initial absorbance was about 0.1 for both versions of the enzyme at day 106. The results were presented in FIG. 4. Again good linearity was shown for a glucose concentration of up to 1,000 mg/dL.

Figure 5:
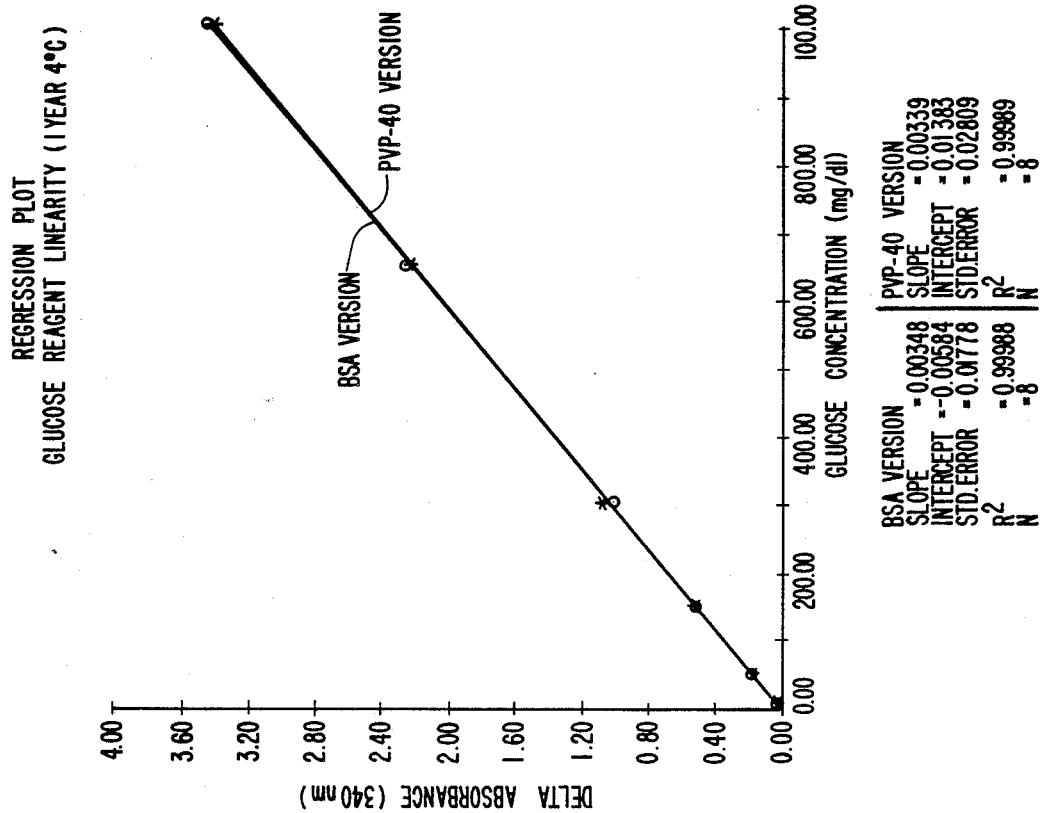

In a separate real time linearity study, the same procedure was repeated for the two versions of the enzyme solution after they have been stored at 4° C. for about one year. Although the initial absorbance increased to 0.17, the linearity remained excellent. FIG. 5 is a plot of the delta absorbance vs. glucose concentration for both versions of the enzyme solution. Linearity was excellent up to 1,000 mg/dL.

Figure 6:
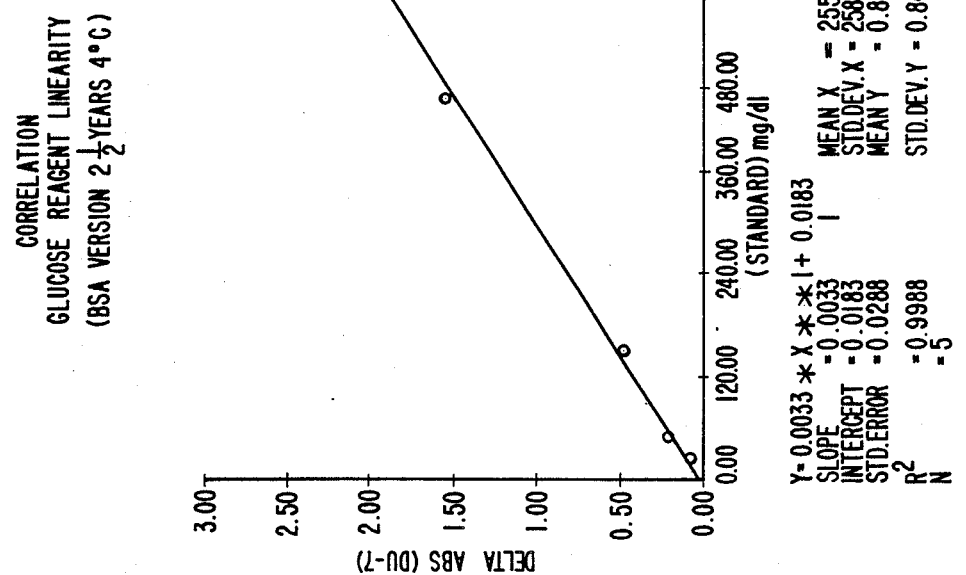

In a 2½ year real time linearity study, the same procedure was repeated for the BSA version of the enzyme solution, stored at 4° C. for about 2½ years. NERL glucose standards having glucose concentrations of 25, 50, 150, 450 and 600 mg/dL, respectively, were used. The initial absorbance increased to 0.21 (2½ years) from 0.17 (one year). However, as shown in FIG. 6, which is plot of the absorbance difference vs. glucose concentration, the linearity is excellent up to 600 mg/dL.

EXAMPLE 3

Optimization of Reagent Components

The effects of changes in the concentration of each of the enzymes (HK and G-6-PDH) and coenzymes (ATP and NAD) of the $T(\frac{1}{2})$, while the other reagent components were kept constant (as provided in the formulations above), were studied using the glucose assay above, using a laboratory prepared glucose standard with a glucose level of 650 mg/dL. The BSA version of the enzyme solution was used in this optimization study.

FIGS. 7, 8, 9, 10 show the effect of reagent component on $T(\frac{1}{2})$. The results showed that the enzyme and coenzyme component concentrations used in the formulations provided above fall within the optimal range. For both HK ad G-6-PDH, the higher the enzyme concentration, the faster the reaction and therefore the shorter the T(½). The optimization is based substantially on a balance between cost and the rate of reaction.

EXAMPLE 4

Real Time Stability Study

The two versions of the enzyme solution were stored at 4° C. over a period of about 2½ years. Glucose assays were run using the enzyme solutions at 1 and 2½ years, respectively. The reaction profiles were followed by scans of the absorbance at 340 nm vs. time (seconds). For the one year study, laboratory prepared glucose standards of 150 and 650 mg/dL glucose concentration were used. For the 2½ year study, a NERL glucose standard with a glucose concentration of 500 mg/dL was used. FIGS. 11–15 are scans of the reaction profiles at 1 year and 2½ years. The time of one-half reaction was also determined in all of the assays performed.

Table 2 compares the time of one-half reaction, T(½), and time of substantial completion of reaction (end point) for the enzyme reagent of the subject invention, stored at 4° C. for periods up to 2½ years.

TABLE 2

Real Time Stability Study

| Storage Time | Antioxidant | Glucose Concentration (mg/L) | Initial ABS | T (½) (sec.) | End Point (min.) |
|---|---|---|---|---|---|
| day 0 | BSA or PVP-40 | 500 | 0.12 | 15 | 0.5 |
| 1 year | BSA | 150 | 0.17 | 17 | 1 |
| 1 year | BSA | 650 | 0.17 | 17 | 1.5 |
| 1 year | PVP-40 | 150 | 0.17 | 19 | 1 |
| 1 year | PVP-40 | 650 | 0.17 | 19 | 1.5 |
| 2½yr. | BSA | 500 | 0.21 | 19.75 | 2 |

The enzyme reagent of the present invention has many advantages. The projected shelf life, when the enzyme reagent is stored properly at 4° C., can be more than 15 years. This means that the reagent can withstand occasional mishandling during storage or transit. The shelf life at room temperature can be up to 1½ years. Reaction is complete within two minutes for a 500 mg/dL glucose standard. The end point stability is up to 5 minutes. This allows for very rapid quantitative determination of glucose. The initial blank is low, allowing for greater sensitivity. The linearity of the reagent is excellent up to about 1,000 mg glucose/dL. The calculated sensitivity for this BSA version of this reagent using a 500 mg/dL standard is 0.0032 Abs/mg/dL in a 1 cm cuvette path length, at 340 nm.

The homogeneity of the stable liquid enzyme reagent of this invention also solves the problems of prior art glucose enzyme reagents, especially the problems with reagent handling, and with quality control of the assays. The enzyme reagent of this invention can be pipetted and aliquoted easily since there are no liquid suspensions such as that in the ammonium sulfate stabilized enzyme reagent. Assay results are reproducible using this enzyme reagent. The enzyme reagent of the present invention is easily adapted for both manual use and for automated analyzers.

Although the present invention has been described in considerable detail with reference to certain preferred versions thereof, other versions are possible. Therefore, the spirit and scope of the appended claims should not necessarily be limited to the description of the preferred versions thereof.

What is claimed is:

1. A homogeneous liquid enzyme reagent for use for the quantitative determination of glucose in a glucose assay using adenosine triphosphate and nicotinamide-adenine dinucleotide as coenzymes, the coenzymes being in excess, reaction between glucose and adenosine triphosphate being catalyzed by the enzyme hexokinase in the presence of magnesium ions, the enzyme reagent comprising:
   (a) at leaast about 60% v/v of water;
   (b) a water-miscible polyol organic solvent in an amount of from about 20% to about 40% v/v;
   (c) hexokinase enzyme;
   (d) glucose-6-phosphate dehydrogenase enzyme; and
   (e) a stabilizer system comprising a metal ion chelating agent in a sufficient amount of at least 0.5 mM such that the amount of chelating agent is no no more than about half ot the amount of magnesium ions present on a molar basis and the enzyme reagent has a shelf life of at least two years when stored at a temperature in the range of from about 2° to about 8° C.

2. The enzyme reagent of claim 1 wherein the chelating agent is ethylenediaminetetraacetic acid.

3. The enzyme reagent of claim 1 wherein the stabilizer system also comprises an antioxidant.

4. The enzyme reagent of claim 3 wherein the antioxidant is bovine serum albumin in an amount of at least 2 g per liter.

5. The enzyme reagent of claim 3 wherein the antioxidant comprises polyvinylpyrrolidone-40 in an amount of at least about 2 g per liter, and N-acetyl cysteine in an amount of at least about 0.4 g per liter.

6. The enzyme reagent of claim 1 wherein the stabilizer system also comprises a microbio-control agent.

7. The enzyme reagent of claim 6 wherein the microbio-control agent is sodium azide in an amount of at least about 0.25 g per liter.

8. The enzyme reagent of claim 4 wherein the organic polyol solvent is glycerol, the enzyme reagent comprising:
   (a) hexokinase enzyme in an amount of from about from 6 to about 80 KIU per liter;
   (b) glucose-6-phosphate dehydrogenase enzyme in an amount of from about 3 to about 60 KIU per liter;
   (c) bovine serum albumin, in an amount of from about 2 to about 8 g per liter;
   (d) ethylenediaminetetraacetic acid in an amount of from about 0.5 to about 5 mM;
   (e) sodium azide in an amount of from about 0.25 to about 1.0 g per liter; and
   (f) TRIS-HCl buffer, in an amount of from 0.05 to about 0.2 mM;
   wherein the pH of the enzyme reagent is adjusted to about 7.5.

9. The enzyme reagent of claim 5 wherein the organic polyol solvent is glycerol, the enzyme reagent comprising;
   (a) hexokinase enzyme in an amount of from about 6 to about 80 KIU per liter;
   (b) glucose-6-phosphate dehydrogenase system in an amount of from about 3 to about 60 KIU per liter;
   (c) polyvinylpyrrolidone-40 in an amount of from about 2 to about 8 g per liter, and N-acetyl cysteine in an amount of from about 0.4 to about 1.6 g per liter;
   (d) ethylenediaminetetraacetic acid, in an amount of from about 0.50 to about 5 mM;

(e) sodium azide, in an amount of from about 0.25 to about 1.0 g per liter; and
(f) TRIS-HCl buffer, in an amount of from about 0.05 to about 0.2 mM;
wherein the pH of the enzyme reagent is adjusted to about 7.5.

10. The enzyme reagent of claim 8 wherein shelf life of the enzyme reagent is defined by the maximum period of storage during which the end point for a glucose assay procedure is reached in no more than about ten minutes when the enzyme reagent is used in the glucose assay procedure and mixed with a liquid coenzyme reagent comprising magnesium ions and the coenzymes adenosine triphosphate and nicotinamide-adenine dinucleotide, and with a test sample comprising glucose to form an assay reaction mixture, the volume ratio of enzyme reagent:coenzyme reagent:test sample being about 100:1000:11, the glucose concentration in the test sample being between about 10 to about 500 mg per deciliter, the coenzymes in the reaction mixture being in excess for the glucose assay relative to the glucose concentration in the reaction mixture, and the chelating agent concentration in the reaction mixture being no more than about 50% of the magnesium ion concentration in the reaction mixture.

11. The enzyme reagent of claim 10 wherein hexokinase is in an amount of from about 15 to about 35 KIU per liter, glucose-6-phosphate dehydrogenase is in an amount of from about 20 to about 35 KIU per liter, and wherein the molar ratio of adenosine triphosphate to glucose is more than about 3:1 in the reaction mixture, and the molar ratio of nicotinamide adenine dinucleotide to glucose in the reaction mixture is more than about 5:1, and the end point for the assay can be reached in no more than about two minutes.

12. The enzyme reagent of claim 9 wherein shelf life of the enzyme reagent is defined by the maximum period of storage during which the end point for a glucose assay procedure is reached in no more than about ten minutes when the enzyme reagent is used in the glucose assay procedure and mixed with a liquid coenzyme reagent comprising magnesium ions and the coenzymes adenosine triphosphate and nicotinamide-adenine dinucleotide, and with a test sample comprising glucose to form an assay reaction mixture, the volume ratio of enzyme reagent:coenzyme reagent:test sample being about 100:1000:11, the glucose concentration in the test sample being between about 10 to about 500 mg per deciliter, the coenzymes in the reaction mixture being in excess for the glucose assay relative to the glucose concentration in the reaction mixture, and the chelating agent concentration in the reaction mixture being no more than about 50% of the magnesium ion concentration in the reaction mixture.

13. The enzyme reagent of claim 12 wherein hexokinase is in an amount of from about 15 to about 35 KIU per liter, glucose-6-phosphate dehydrogenase is in an amount of from about 20 to about 35 KIU per liter, and wherein the molar ratio of adenosine triphosphate to glucose in the reaction mixture is more than about 3:1, and the molar ratio of nicotinamide adenine dinucleotide to glucose in the reaction mixture is more than about 5:1, and the end point for the assay can be reached in no more than about two minutes.

14. The enzyme reagent of claim 8 wherein shelf life of the enzyme reagent is defined by the maximum period of storage during which the time of one-half reaction for a glucose end point assay is no more than about 1.5 times the time of one-half reaction for the identical assay when the enzyme reagent was initially prepared when the enzyme reagent is used in the glucose assay procedure and mixed with a liquid coenzyme reagent comprising magnesium ions and the coenzymes adenosine triphosphate and nicotinamide-adenine dinucleotide, and with a test sample comprising glucose to form an assay reaction mixture, the volume ratio of enzyme reagent:coenzyme reagent:test sample being about 100:1000:11, the glucose concentration in the test sample being between about 10 to about 500 mg per deciliter, the coenzymes in the reaction mixture being in excess for the glucose assay relative to the glucose concentration in the reaction mixture and the chelating agent concentration in the reaction mixture being no more than about 50% of the magnesium ion concentration in the reaction mixture.

15. The enzyme reagent of claim 9 wherein shelf life of the enzyme reagent is defined by the maximum period of storage during which the time of one-half reaction for a glucose end point assay is no more than about 1.5 times the time of one-half reaction for the identical assay when the enzyme reagent was initially prepared when the enzyme reagent is used in the glucose assay procedure and mixed with a liquid coenzyme reagent comprising magnesium ions and the coenzymes adenosine triphosphate and nicotinamide-adenine dinucleotide, and with a test sample comprising glucose to form an assay reaction mixture, the volume ratio of enzyme reagent: coenzyme reagent; test sample being about 100:1000:11, the glucose concentration in the test sample being between about 10 to about 500 mg per deciliter, the coenzymes in the reaction mixture being in excess for the glucose relative to the glucose concentration in the reaction mixture and the chelating agent concentration in the reaction mixture being no more than about 50% of the magnesium ion concentration in the reaction mixture.

16. A kit of reagents for use for the quantitative determination of glucose in a glucose assay, the kit comprising, in in at least two containers:
(a) a homogenous liquid enzyme reagent comprising:
(i) at least about 60% v/v of water;
(ii) a water-miscible polyol organic solvent in an amount of from about 20 to about 40% v/v;
(iii) hexokinase enzyme;
(iv) glucose-6-phosphate dehydrogenase enzyme; and
(v) a stabilizer system comprising a metal ion chelating agent in a sufficient amount of at least about 0.5 mM such that the enzyme reagent has a shelf life of at least two years when stored at a temperature in the range of from about 2° to about 8° C.;
(b) a homogeneous liquid coenzyme reagent comprising:
(i) at least about 60% v/v of water;
(ii) a water-miscible polyol organic solvent in an amount of from about 5 to about 20% v/v;
(iii) adenosine triphosphate coenzyme;
(iv) nicotinamide-adenine dinucleotide coenzyme; and
(v) magnesium ions:
the enzyme and coenzyme reagents being formulated such that when they are mixed together to form a combined reagent suitable for performing the glucose assay, in the combined reagent the amount of chelating agent from the enzyme reagent is no more than about half of the amount of magnesium ions from the coenzyme reagent, on a molar basis.

17. The kit of claim 16 wherein the combined reagent is formed by mixing 1:10 v/v of the enzyme and coenzyme reagents, and wherein in the combined reagent the amount of chelating agent from the enzyme reagent is no more than about one-tenth the amount of magnesium ions from the coenzyme reagent, on a molar basis.

18. The kit of claim 16 wherein the chelating agent is ethylenediaminetetraacetic acid.

19. The kit of claim 16 wherein the stabilizer system also comprises an antioxidant.

20. The kit of claim 19 wherein the antioxidant is bovine serum albumin in an amount of at least 2 g per liter.

21. The kit of claim 19 wherein the antioxidant comprises polyvinylpyrrolidone-40 in an amount of at least about 2 g per liter, and N-acetyl cysteine in an amount of at least about 0.4 g per liter.

22. The kit of claim 16 wherein the stabilizer system also comprises a microbio-control agent.

23. The kit of claim 22 wherein the microbio-control agent is sodium azide in an amount of at least about 0.25 g per liter.

24. The kit of claim 20 wherein the organic polyol solvent is glycerol, the enzyme reagent comprising:
   (a) hexokinase enzyme in an amount of from about 6 to about 80 KIU per liter;
   (b) glucose-6-phosphate dehydrogenase enzyme in an amount of from about 3 to about 60 KIU per liter;
   (c) bovine serum albumin, in an amount of from about 2 to about 8 g per liter;
   (d) ethylenediaminetetraacetic acid in an amount of from about 0.5 to about 5 mM;
   (e) sodium azide in an amount of from about 0.25 to about 1.0 g per liter; and
   (f) TRIS-HCl buffer, in an amount of from about 0.05 to about 0.2 mM;
   wherein the pH of the enzyme reagent is adjusted to about 7.5.

25. The kit of claim 21 wherein the organic polyol solvent is glycerol, the enzyme reagent comprising;
   (a) hexokinase enzyme in an amount of from about 6 to about 80 KIU per liter;
   (b) glucose-6-phosphate dehydrogenase enzyme in an amount of from about 3 to about 60 KIU per liter;
   (c) polyvinylpyrrolidone-40 in an amount of from about 2 to about 8 g per liter, and N-acetyl cysteine in an amount of from about 0.4 to about 1.6 g per liter;
   (d) ethylenediaminetetraacetic acid, in an amount of from about 0.5 to about 5 mM;
   (e) sodium azide, in an amount of from about 0.25 to about 1.0 g per liter; and
   (f) TRIS-HCl buffer, in an amount of from about 0.05 to about 0.2 mM;
   wherein the pH of the enzyme reagent is adjusted to about 7.5.

26. The kit of claim 24 wherein shelf life of the enzyme reagent is defined by the maximum period of storage during which the end point for a glucose assay procedure is reached in no more than about ten minutes when the enzyme reagent is used in the glucose assay and mixed with the coenzyme reagent and a test sample containing glucose to form an assay reaction mixture, the volume ratio of enzyme reagent:coenzyme reagent:test sample being about 100:1000:11, the glucose concentration in the test sample being between about 10 to about 500 mg per deciliter, the coenzymes in the reaction mixture being in excess for the glucose assay relative to the glucose concentration in the reaction mixture, and the chelating agent concentration in the reaction mixture being no more than about 50% of the magnesium ion concentration in the reaction mixture.

27. The kit of claim 26 wherein hexokinase is in an amount of from about 15 to about 35 KIU per liter, glucose-6-phosphate dehydrogenase is in an amount of from about 20 to about 35 KIU per liter, and wherein the molar ratio of adenosine triphosphate to glucose is more than about 3:1, and the molar ratio of nicotinamide adenine dinucleotide to glucose in the reaction mixture is more than about 5:1, and the end point for the assay can be reached in no more than about two minutes.

28. The kit of claim 25 wherein shelf life of the enzyme reagent is defined by the maximum period of storage during which the end point for a glucose assay procedure is reached in no more than about ten minutes when the enzyme reagent is used in the glucose assay and mixed with the coenzyme reagent and a test sample containing glucose to form an assay reaction mixture, the volume ratio of enzyme reagent:coenzyme reagent:test sample being about 100:1000:11, the glucose concentration in the test sample being between about 10 to about 500 mg per deciliter, the coenzymes in the reaction mixture being in excess for the glucose assay relative to the glucose concentration in the reaction mixture, and the chelating agent concentration in the reaction mixture being no more than about 50% of the magnesium ion concentration in the reaction mixture.

29. The kit of claim 28 wherein hexokinase is in an amount of from about 15 to about 35 KIU per liter, glucose-6-phosphate dehydrogenase is in an amount of from about 20 to about 35 KIU per liter, and wherein the molar ratio of adenosine triphosphate to glucose in the reaction mixture is more than about 3:1, and the molar ratio of nicotinamide adenine dinucleotide to glucose in the reaction mixture is more than about 5:1, and the end point for the assay can be reached in no more than about two minutes.

30. The kit of claim 24 wherein shelf life of the enzyme reagent is defined by the maximum period of storage during which the time of one-half reaction for a glucose end assay is no more than about 1.5 times the time of one-half reaction for the identical assay when the enzyme reagent was initially prepared when the enzyme reagent is used in the glucose assay procedure and mixed with a liquid coenzyme reagent comprising magnesium ions and the coenzymes adenosine triphosphate and nicotinamide-adenine dinucleotide, and with a test sample comprising glucose to form an assay reaction mixture, the volume ratio of enzyme reagent:coenzyme reagent:test sample being about 100:1000:11, the glucose concentration in the test sample being between about 10 to about 500 mg per deciliter, the coenzymes in the reaction mixture being in excess for the glucose assay relative to the glucose concentration in the reaction mixture, and the chelating agent concentration in the reaction mixture being no more than about 50% of the magnesium ion concentration in the reaction mixture.

31. The kit of claim 25 wherein shelf life of the enzyme reagent is defined by the maximum period of storage during which the time of one-half reaction for a glucose end point assay is no more than about 1.5 times the time of one-half reaction for the identical assay when the enzyme reagent was initially prepared when the enzyme reagent is used in the glucose assay procedure and mixed with a liquid coenzyme reagent comprising magnesium ions and the coenzymes adenosine triphosphate and nicotinamide-adenine dinucleotide, and with a test sample comprising glucose to form an assay reaction mixture, the volume ratio of enzyme reagent:coenzyme reagent:test sample being about 100:1000:11, the glucose concentration in the test sample being between about 10 to about 500 mg per deciliter, the coenzymes in the reaction mixture being in excess for the glucose assay relative to the glucose concentration in the reaction mixture, and the chelating agent concentration in the reaction mixture being no more than about 50% of the magnesium ion concentration in the reaction mixture.

32. A method for the quantitative determination of glucose comprising the steps of:
 (a) mixing:
   (i) a test sample comprising glucose;
   (ii) a homogeneous liquid enzyme reagent, the enzyme reagent comprising:
     A. at least about 60% v/v of water;
     B. a water-miscible polyol organic solvent in an amount of from about 20 to about 40% v/v;
     C. hexokinase enzyme;
     D. glucose-6-phosphate dehydrogenase enzyme; and
     E. a stabilizer system comprising a metal ion chelating agent in a sufficient amount of at least about 0.5 mM such that the enzyme reagent has a shelf life of at least two years when stored at a temperature in the range of from about 2° to about 8° C.; and
   (iii) a homogeneous coenzyme reagent comprising:
     A. at least about 80% v/v of water;
     B. a water-miscible polyol organic solvent in an amount of from about 5 to about 20% v/v;
     C. adenosine triphosphate coenzyme;
     D. nicotinamide-adenine dinucleotide coenzyme; and
     E. magnesium ions;
 to form an assay reaction mixture, the reagents and test sample being mixed in such proportions that the amount of chelating agent from the enzyme reagent is no more than about half of the amount of magnesium ions from the coenzyme reagent, on a molar basis; and
 (b) measuring the formation of reduced nicotinamide-adenine dinucleotide.

33. The method of claim 32 wherein the mixing steps comprising first mixing 1:10 v/v of the enzyme and coenzyme reagents to form a combined reagent and wherein in the combined reagent the amount of chelating agent from the enzyme reagent is no more than about one-tenth the amount of magnesium ions from the coenzyme reagent.

34. The method of claim 32 wherein the chelating agent is ethylenediaminetetraacetic acid.

35. The method of claim 32 wherein the stabilizer system also comprises an antioxidant.

36. The method of claim 35 wherein the antioxidant is bovine serum albumin in an amount of at least 2 g per liter.

37. The method of claim 35 wherein the antioxidant comprises polyvinylpyrrolidone-40 in an amount of at least about 2 g per liter, and N-acetyl cysteine in an amount of at least about 0.4 g per liter.

38. The method of claim 32 wherein the stabilizer system also comprises a microbio-control agent.

39. The method of claim 38 wherein the microbio-control agent is sodium azide in an amount of at least about 0.25 g per liter.

40. The method of claim 36 wherein the organic polyol solvent is glycerol, the enzyme reagent comprising:
 (a) hexokinase enzyme in an amount of from about 6 to about 80 KIU per liter;
 (b) glucose-6-phosphate dehydrogenase enzyme in an amount of from about 3 to about 60 KIU per liter;
 (c) bovine serum albumin, in an amount of from about 2 to about 8 g per liter;
 (d) ethylenediaminetetraacetic acid in an amount of from about 0.5 to about 5 mM;
 (e) sodium azide in an amount of from about 0.25 to about 1.0 g per liter; and
 (f) TRIS-HCl buffer, in an amount of from about 0.05 to about 0.2 mM;
wherein the pH of the enzyme reagent is adjusted to about 7.5.

41. The method of claim 37 wherein the organic polyol solvent is glycerol, the enzyme reagent comprising:
 (a) hexokinase enzyme in an amount of from about 6 to about 80 KIU per liter;
 (b) glucose-6-phosphate dehydrogenase enzyme in an amount of from about 3 to about 60 KIU per liter;
 (c) polyvinlypyrrolidone-40 in an amount of from about 2 to about 8 g per liter, and N-acetyl cysteine in an amount of from about 0.4 to about 1.6 per liter;
 (d) ethylenediaminetetraacetic acid, in an amount of from about 0.5 to about 5 mM;
 (e) sodium azide, in an amount of from about 0.25 to about 1.0 g per liter; and
 (f) TRIS-HCl buffer, in an amount of from about 0.05 to about 0.2 mM;
wherein the pH of the enzyme reagent is adjusted to about 7.5.

42. The method of claim 40 wherein shelf life of the enzyme reagent is defined by the maximum period of storage during which the end point for the glucose assay is reached in no more than about ten minutes when the enzyme reagent is used in the glucose assay and mixed with the coenzyme reagent and a test sample comprising glucose to form an assay reaction mixture, the volume ratio of enzyme reagent:coenzyme reagent:test sample being about 100:1000:11, the glucose concentration in the test sample being between about 10 to about 500 mg per deciliter, the coenzymes in the reaction mixture being in excess for the glucose assay relative to the glucose concentration in the reaction mixture, and the chelating agent concentration in the reaction mixture being no more than about 50% of the magnesium ion concentration in the reaction mixture.

43. The method of claim 42 wherein hexokinase is in an amount of from about 15 to about 35 KIU per liter, glucose-6-phosphate dehydrogenase is in an amount of from about 20 to about 35 KIU per liter, and wherein the molar ratio of adenosine triphosphate to glucose in the reaction mixture is more than about 3:1, and the molar ratio of nicotinamide adenine dinucleotide to glucose in the reaction mixture is more than about 5:1, and the end point for the assay can be reached in no more than about two minutes.

44. The method of claim 41 wherein shelf life of the enzyme reagent is defined by the maximum period of storage during which the end point for the glucose assay is reached in no more than about ten minutes when the enzyme reagent is used in the glucose assay and mixed with the coenzyme reagent and a test sample comprising glucose to form an assay reaction mixture the volume ratio of enzyme reagent:coenzyme reagent:test sample being about 100:1000:11, the glucose concentration in the test sample being between about 10 to about 500 mg per deciliter, the coenzymes in the reaction mixture being in excess for the glucose assay relative to the glucose concentration in the reaction mixture, and the chelating agent concentration in the reaction mixture being no more than about 50% of the magnesium ion concentration in the reaction mixture.

45. The method of claim 44 wherein hexokinase is in an amount of from about 15 to about 35 KIU per liter, glucose-6-phosphate dehydrogenase is in an amount of from about 20 to about 35 KIU per liter, and wherein the molar ratio of adenosine triphosphate to glucose in the reaction mixture is more than about 3:1, and the molar ratio of nicotinamide adenine dinucleotide to glucose in the reaction mixture is more than about 5:1, and the end point for the assay can be reached in no more than about two minutes.

46. The method of claim 40 wherein shelf life of the enzyme reagent is defined by the maximum period of storage during which the time of one-half reaction for a glucose end point assay is no more than about 1.5 times the time of one-half reaction for the identical assay when the enzyme reagent was initially prepared when the enzyme reagent is used in the glucose assay procedure and mixed with a liquid coenzyme reagent comprising magnesium ions and the coenzymes adenosine triphosphate and nicotinamide-adenine dinucleotide, and with a test sample comprising glucose to form an assay reaction mixture, the volume ratio of enzyme reagent:coenzyme reagent:test sample being about 100:1000:11, the glucose concentration in the test sample being between about 10 to about 500 mg per deciliter, the coenzymes in the reaction mixture being in excess for the glucose assay relative to the glucose concentration in the reaction mixture, and the chelating agent concentration in the reaction mixture being no more than about 50% of the magnesium in concentration in the reaction mixture.

47. The method of claim 41 wherein shelf life of the enzyme reagent is defined by the maximum period of storage during which the time of one-half reaction for a glucose end point assay is no more than about 1.5 times the time of one-half reaction for the identical assay when the enzyme reagent was initially prepared when the enzyme reagent is used in the glucose assay procedure and mixed with a liquid coenzyme reagent comprising magnesium ions and the coenzymes adenosine triphosphate and nicotinamide-adenine dinucleotide, and with a test sample comprising glucose to form an assay reaction mixture, the volume ratio of enzyme reagent:coenzyme reagent:test sample being about 100:1000:11, the glucose concentration in the test sample being between about 10 to about 500 mg per deciliter, the coenzymes in the reaction mixture being in excess for the glucose assay relative to the glucose concentration in the reaction mixture, and the chelating agent concentration in the reaction mixture being no more than about 50% of the magnesium ion concentration in the reaction mixture.

* * * * *

UNITED STATES PATENT AND TRADEMARK OFFICE
CERTIFICATE OF CORRECTION

PATENT NO. : 4,897,346

DATED : January 30, 1990

INVENTOR(S) : THOMAS H. GAWRONSKI

It is certified that error appears in the above-identified patent and that said Letters Patent is hereby corrected as shown below:

Column 14,

In claim 9, line 61, delete "system" and insert --enzyme--.

Column 18,

In claim 30, line 46, after "end" insert --point--.

Signed and Sealed this

Fourteenth Day of September, 1993

Attest:

BRUCE LEHMAN

Attesting Officer

Commissioner of Patents and Trademarks